US009733214B2

(12) United States Patent
Hunter et al.

(10) Patent No.: US 9,733,214 B2
(45) Date of Patent: Aug. 15, 2017

(54) RAPID LC MAPPING OF COV VALUES FOR SELEXION™ TECHNOLOGY USING MRM-TRIGGERED MRM FUNCTIONALITY

(71) Applicant: DH Technologies Development Pte. Ltd., Singapore (SG)

(72) Inventors: Christie L. Hunter, Redwood City, CA (US); David M. Cox, North York (CA)

(73) Assignee: DH Technologies Development Pte. Ltd., Singapore (SG)

( * ) Notice: Subject to any disclaimer, the term of this patent is extended or adjusted under 35 U.S.C. 154(b) by 0 days.

(21) Appl. No.: 15/107,455

(22) PCT Filed: Feb. 10, 2015

(86) PCT No.: PCT/IB2015/000132
§ 371 (c)(1),
(2) Date: Jun. 22, 2016

(87) PCT Pub. No.: WO2015/124982
PCT Pub. Date: Aug. 27, 2015

(65) Prior Publication Data
US 2016/0349210 A1 Dec. 1, 2016

Related U.S. Application Data

(60) Provisional application No. 61/942,138, filed on Feb. 20, 2014.

(51) Int. Cl.
*H01J 49/00* (2006.01)
*G01N 27/62* (2006.01)
*G01N 30/72* (2006.01)

(52) U.S. Cl.
CPC ....... *G01N 27/622* (2013.01); *G01N 30/7233* (2013.01); *H01J 49/004* (2013.01); *H01J 49/0027* (2013.01)

(58) Field of Classification Search
CPC ..... G01N 27/622; G01N 27/624; H01J 49/00; H01J 49/02; H01J 49/0027; H01J 49/0031; H01J 49/0036
(Continued)

(56) References Cited

U.S. PATENT DOCUMENTS 8,026,479 B2    9/2011  Lock et al.
2006/0289745 A1  12/2006  Miller et al.
(Continued)

OTHER PUBLICATIONS

International Search Report and Written Opinion for PCT/IB2015/000132, mailed Jun. 2, 2015.

*Primary Examiner* — Jason McCormack
(74) *Attorney, Agent, or Firm* — John R. Kasha; Kelly L. Kasha; Kasha Law LLC (57) ABSTRACT

MRM triggered MRM, where the triggered MRM transitions make use of mobility device parameter values for the same compound, is performed. A plurality of primary MRM transitions are received and stored together with a mobility device parameter value for each transition as an MRM cycle list. Control information instructs a mobility device and a mass spectrometer to interrogate each MRM transition on the MRM cycle list within an MRM cycle of the mass spectrometer. If a product ion intensity value of an MRM transition exceeds a threshold value for a primary MRM transition, a plurality of secondary MRM transitions of the primary MRM transition with different mobility device parameter values are added to the MRM cycle list. The intensities of the measured secondary MRM transitions provide information on the optimum mobility device parameter for each compound.

20 Claims, 4 Drawing Sheets

(58) Field of Classification Search
USPC ....... 250/281, 282, 283, 286, 290, 292, 293, 250/299
See application file for complete search history.

(56) References Cited

U.S. PATENT DOCUMENTS

| | | |
|---|---|---|
| 2011/0248160 A1 | 10/2011 | Belov |
| 2012/0241602 A1 | 9/2012 | Goshawk et al. |
| 2013/0289894 A1* | 10/2013 | Cox .................... H01J 49/0031 702/23 |

\* cited by examiner

RAPID LC MAPPING OF COV VALUES FOR SELEXION™ TECHNOLOGY USING MRM-TRIGGERED MRM FUNCTIONALITY

CROSS REFERENCE TO RELATED APPLICATION

This application claims the benefit of U.S. Provisional Patent Application Ser. No. 61/942,138, filed Feb. 20, 2014, the content of which is incorporated by reference herein in its entirety.

INTRODUCTION

When using a mobility separation device, such as the SelexION™ device (a form of differential mobility separation or DMS), for analysis of specific compounds, parameters of the mobility device must be tuned for each compound to get maximal transmission and sensitivity. An exemplary parameter of a DMS device is the compensation voltage (CoV). The CoV is dependent on compound characteristics and does have some variability with experimental conditions, therefore tuning of the CoV under specific sample introduction conditions helps with finding the value for the experimental conditions to be used. Sample introduction conditions such as liquid chromatography (LC), capillary electrophoresis (CE), or flow injection analysis (FIA) are examples of such sample introduction conditions that might be used in combination with a mobility device.

Some compound dependent parameters used by mass spectrometer devices other than mobility devices can be predicted. However, the prediction of compound dependent CoV values for a DMS device is something that the mass spectrometry industry has been unable to obtain. As a result, the industry has conventionally interrogated a large CoV range for compounds of interest. In other words, a large number of different CoV values (such as 20-30) have been conventionally interrogated for each compound, meaning only one or two compounds can be tested per injection.

Using strategies that can extend the number of compound dependent parameters that can be interrogated in a single run such as time scheduling of multiple reaction monitoring transitions (MRM or SRM) can be used to increase this number by a small amount. However, for some markets where larger panels of analytes (more than 20 analytes) are analyzed, this could make assay development a very slow process. In applied markets and omics markets more than 50 analytes per run are routinely monitored by MRM in complex matrices. To date the industry has been unable to obtain a strategy that can more efficiently interrogate and optimize a broader range of compound dependent parameters for mobility devices in less time and using fewer sample injections.

SUMMARY

A system is disclosed for performing multiple reaction monitoring (MRM) triggered MRM, where the triggered MRM transitions make use of different compound dependent parameters such as the mobility device parameter values for the same compound. The system includes an ion source, a mobility device, a mass spectrometer, and a processor in communication with the mass spectrometer and the mobility device. The ion source ionizes a sample producing an ion beam. The system can also include a sample introduction device that presents the sample to the ion source. The mobility device receives the ion beam from the ion source and is adapted to accept a mobility device parameter value that causes the mobility device to select ions from the ion beam based on the mobility device parameter value. The mass spectrometer is adapted to receive selected ions from the mobility device and perform MRM scans on the received ions.

The processor performs a number of steps. In step (a), the processor receives one or more MRM precursor ion to product ion transitions for one or more compounds from a user, producing a plurality of primary MRM transitions. In step (b), for each transition of the plurality of primary MRM transitions, the processor creates and stores a plurality of secondary MRM precursor ion to product ion transitions that each include the same precursor ion to product ion transition as the primary MRM transition but have different mobility device parameter values. In step (c), the processor creates and stores an MRM cycle list that initially includes the plurality of primary MRM transitions and an initial mobility device parameter value for each transition of the plurality of primary MRM transitions.

In a conventional MRM method, repeated cycles of scans are performed by a mass spectrometer for predetermined compounds of interest. An MRM scan, or MRM measurement, involves selecting a precursor ion for fragmentation and monitoring the fragmentation for a specific fragment ion, or product ion. An MRM transition is, therefore, a transition from a precursor ion to a specific product ion. The time it takes to monitor one MRM transition, or one MRM scan, is the scan time, for example. A "cycle" includes a list of MRM transitions for compounds to be cycled through and scanned for by the mass spectrometer. This list can be called the MRM cycle list. The MRM cycle time is, therefore, the sum of the scan times for the MRM transitions on the MRM cycle list.

In step (d), the processor sends control information, including the MRM cycle list, to the mobility device and the mass spectrometer instructing the mobility device and the mass spectrometer to interrogate each MRM transition on the MRM cycle list within a single cycle of the mass spectrometer. Each MRM transition is interrogated by applying the mobility device parameter value of the MRM transition to the mobility device and performing an MRM scan using the mass spectrometer.

An MRM scan, or MRM measurement, involves selecting a precursor ion for fragmentation and monitoring the fragmentation for a specific fragment ion, or product ion. An MRM transition is, therefore, a transition from a precursor ion to a specific product ion. The time it takes to monitor one MRM transition, or one MRM scan, is the scan time, for example. A "cycle" includes a list of MRM transitions for compounds to be cycled through and scanned for by the mass spectrometer. This list can be called the MRM cycle list. The MRM cycle time is, therefore, the sum of the scan times for the MRM transitions on the MRM cycle list. In an MRM method, a cycle of scans is generally repeatedly performed by a mass spectrometer for the predetermined compounds of interest on the cycle list.

In step (e), the processor receives a product ion intensity value from the mass spectrometer for each MRM transition and stores the product ion intensity value with a primary or secondary MRM transition represented by the MRM transition. In step (f), if a product ion intensity value of an MRM transition exceeds a threshold value and the MRM transition is a primary MRM transition, the processor adds a plurality of secondary MRM transitions of the primary MRM transition to the MRM cycle list and repeats steps (d)-(f). Steps (d)-(f) are repeated for each additional cycle until the number of cycles exceeds a limit, for example.

A method is disclosed for performing MRM triggered MRM that triggers MRM transitions that use different mobility device parameter values for the same compound. The method includes a number of steps. In step (a), one or more MRM precursor ion to product ion transitions are received for one or more compounds from a user using a processor, producing a plurality of primary MRM transitions. In step (b), for each transition of the plurality of primary MRM transitions, a plurality of secondary MRM precursor ion to product ion transitions are created and stored that each include the same precursor ion to product ion transition as the primary MRM transition but have different mobility device parameter values using the processor.

In step (c), an MRM cycle list is created and stored that initially includes the plurality of primary MRM transitions and an initial mobility device parameter value for each transition of the plurality of primary MRM transitions using the processor. In step (d), control information, including the MRM cycle list, is sent to a mobility device and a mass spectrometer instructing the mobility device and the mass spectrometer to interrogate each MRM transition on the MRM cycle list within an MRM cycle of the mass spectrometer using the processor. Each MRM transition is interrogated by applying the mobility device parameter value to the mobility device and performing an MRM scan using the mass spectrometer. The mobility device receives an ion beam from an ion source that ionizes a sample. The mobility device is adapted to accept a mobility device parameter value that causes the mobility device to select ions from the ion beam based on the mobility device parameter value. The mass spectrometer is adapted to receive selected ions from the mobility device and perform MRM scans on the received ions.

In step (e), a product ion intensity value is received from the mass spectrometer for each MRM transition, and the product ion intensity value is stored with a primary or secondary MRM transition represented by the MRM transition using the processor. In step (f), if a product ion intensity value of an MRM transition exceeds a threshold value and the MRM transition is a primary MRM transition, a plurality of secondary MRM transitions (that is, additional MRM transitions that are only monitored if their primary MRM transitions are above a threshold) are added to the MRM cycle list and steps (d)-(f) are repeated using the processor.

A computer program product is disclosed that includes a non-transitory and tangible computer-readable storage medium whose contents include a program with instructions being executed on a processor so as to perform a method for performing MRM triggered MRM that triggers MRM transitions that use different mobility device parameter values for the same compound. The method includes a number of steps. In step (a), a system is provided that includes one or more distinct software modules, and the distinct software modules include an initialization module and a control module. In step (b), the initialization module receives one or more MRM precursor ion to product ion transitions for one or more compounds from a user, producing a plurality of primary MRM transitions.

In step (c), for each transition of the plurality of primary MRM transitions, the initialization module creates and stores a plurality of secondary MRM precursor ion to product ion transitions that each include the same precursor ion to product ion transition as the primary MRM transition but have different mobility device parameter values. In step (d), the initialization module creates and stores an MRM cycle list that initially includes the plurality of primary MRM transitions and an initial mobility device parameter value for each transition of the plurality of primary MRM transitions.

In step (e), the control module sends control information, including the MRM cycle list, to a mobility device and a mass spectrometer instructing the mobility device and the mass spectrometer to interrogate each MRM transition on the MRM cycle list within an MRM cycle of the mass spectrometer. Each MRM transition is interrogated by applying the mobility device parameter value to the mobility device and performing an MRM scan using the mass spectrometer. The mobility device receives an ion beam from an ion source that ionizes a sample. The mobility device is adapted to accept a mobility device parameter value that causes the mobility device to select ions from the ion beam based on the mobility device parameter value. The mass spectrometer is adapted to receive selected ions from the mobility device and perform MRM scans on the received ions.

In step (f) the control module receives a product ion intensity value from the mass spectrometer for each MRM transition and storing the product ion intensity value with a primary or secondary MRM transition represented by the MRM transition. In step (g), if a product ion intensity value of an MRM transition exceeds a threshold value and the MRM transition is a primary MRM transition, the control module adds a plurality of secondary MRM transitions to the MRM cycle list and repeats steps (e)-(g).

BRIEF DESCRIPTION OF THE DRAWINGS

The skilled artisan will understand that the drawings, described below, are for illustration purposes only. The drawings are not intended to limit the scope of the present teachings in any way.

Before one or more embodiments of the present teachings are described in detail, one skilled in the art will appreciate that the present teachings are not limited in their application to the details of construction, the arrangements of components, and the arrangement of steps set forth in the following detailed description or illustrated in the drawings. Also, it is to be understood that the phraseology and terminology used herein is for the purpose of description and should not be regarded as limiting.

DESCRIPTION OF VARIOUS EMBODIMENTS

Computer-Implemented System

Figure 1:
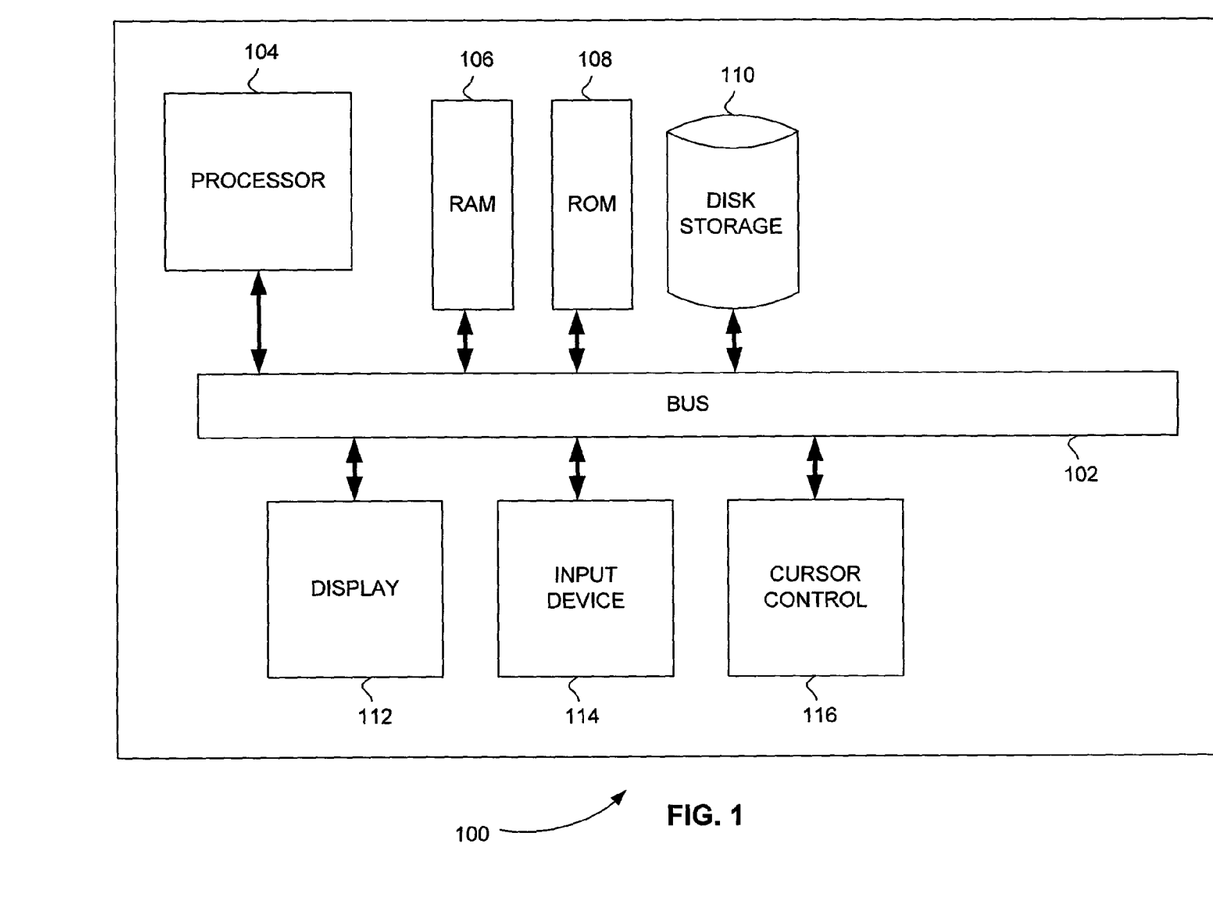
FIG. 1 is a block diagram that illustrates a computer system, upon which embodiments of the present teachings may be implemented.

FIG. 1 is a block diagram that illustrates a computer system 100, upon which embodiments of the present teachings may be implemented. Computer system 100 includes a bus 102 or other communication mechanism for communicating information, and a processor 104 coupled with bus 102 for processing information. Computer system 100 also includes a memory 106, which can be a random access memory (RAM) or other dynamic storage device, coupled to bus 102 for storing instructions to be executed by processor 104. Memory 106 also may be used for storing temporary variables or other intermediate information during execution of instructions to be executed by processor 104. Computer system 100 further includes a read only memory (ROM) 108 or other static storage device coupled to bus 102 for storing static information and instructions for processor 104. A storage device 110, such as a magnetic disk or optical disk, is provided and coupled to bus 102 for storing information and instructions.

Computer system 100 may be coupled via bus 102 to a display 112, such as a cathode ray tube (CRT) or liquid crystal display (LCD), for displaying information to a computer user. An input device 114, including alphanumeric and other keys, is coupled to bus 102 for communicating information and command selections to processor 104. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (i.e., x) and a second axis (i.e., y), that allows the device to specify positions in a plane.

A computer system 100 can perform the present teachings. Consistent with certain implementations of the present teachings, results are provided by computer system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process described herein. Alternatively hard-wired circuitry may be used in place of or in combination with software instructions to implement the present teachings. Thus implementations of the present teachings are not limited to any specific combination of hardware circuitry and software.

The term "computer-readable medium" as used herein refers to any media that participates in providing instructions to processor 104 for execution. Such a medium may take many forms, including but not limited to, non-volatile media, volatile media, and transmission media. Non-volatile media includes, for example, optical or magnetic disks, such as storage device 110. Volatile media includes dynamic memory, such as memory 106. Transmission media includes coaxial cables, copper wire, and fiber optics, including the wires that comprise bus 102.

Common forms of computer-readable media include, for example, a floppy disk, a flexible disk, hard disk, magnetic tape, or any other magnetic medium, a CD-ROM, digital video disc (DVD), a Blu-ray Disc, any other optical medium, a thumb drive, a memory card, a RAM, PROM, and EPROM, a FLASH-EPROM, any other memory chip or cartridge, or any other tangible medium from which a computer can read.

Various forms of computer readable media may be involved in carrying one or more sequences of one or more instructions to processor 104 for execution. For example, the instructions may initially be carried on the magnetic disk of a remote computer. The remote computer can load the instructions into its dynamic memory and send the instructions over a telephone line using a modem. A modem local to computer system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

The following descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

Mobility Device Parameter Value MRM Triggered MRM

As described above, the industry is currently unable to predict differential mobility separation (DMS) device parameter values for a compound. This means that when developing a multiple reaction monitoring (MRM) assay, a large range of parameter values must be interrogated for each compound or analyte, reducing the number of compounds or analytes that can be tested per injection.

In a conventional MRM method, a cycle of scans is repeated by a mass spectrometer for predetermined compounds of interest. An MRM scan involves selecting a precursor ion for fragmentation and monitoring the fragmentation for a specific fragment ion, or product ion. An MRM transition is, therefore, a transition from a precursor ion to a specific product ion. The time it takes to monitor one MRM transition, or one MRM scan, is the scan time, for example. A "cycle" includes a list of MRM transitions for compounds to be cycled through and scanned for by the mass spectrometer. This list can be called the MRM cycle list. The MRM cycle time is, therefore, the sum of the scan times for the MRM transitions on the MRM cycle list.

During the MRM analysis, the mass spectrometer divides its scans among the compounds of interest in the cycle. For example, these scans can be divided equally among the compounds of interest or unequally among the compounds of interest based on a weighting factor. In either case, such cycles have a practical upper limit in the number of compounds that may be scanned for. Once the number of compounds grows too large the amount of scan time available for each compound of interest is insufficient to provide accurate data.

In other words, for example, in order to detect and accurately quantify a compound from a liquid chromatography (LC) run, a minimum number of data points must be obtained across each LC peak. If the number of MRM transitions on an MRM cycle list becomes too large, the cycle time will be too long to be able to perform enough measurements of the MRM cycle list across an LC peak in order to detect and accurately quantify the peak. As a result, there is an upper limit on the number of compounds or number of MRM transitions on an MRM cycle list.

In various embodiments, MRM triggered MRM is used to determine mobility device parameter values for a compound of interest, which is something the industry has been unable to obtain. The mobility device parameter values are determined for compound tuning, for example, which is one aspect of MRM method development. MRM triggered MRM is described, for example, in U.S. Pat. No. 8,026,479. In an MRM triggered MRM method, the MRM cycle list is dynamic and the addition or deletion of an MRM transition from the list is triggered by the results of a previous MRM scan. For example, generally the MRM cycle list includes a set of MRM transitions for a number of different compounds. This initial set of MRM transitions can be called the primary MRM transitions for each compound. If a primary MRM transition of compound is scanned and the product ion of that MRM transition reaches a certain intensity threshold, then this can trigger the addition of one or more different MRM transitions, or secondary MRM transitions, for that compound to the MRM cycle list. These one or more secondary MRM transitions are conventionally used to confirm the presence of the compound, for example.

In various embodiments, the MRM cycle list for compounds in an MRM triggered MRM method includes MRM transitions that have different mobility device parameter values, such as DMS device parameter values. For example, if a MRM transition for a compound on the MRM cycle list for compounds is scanned and the product ion intensity of the MRM transition reaches a certain threshold, then this can trigger the addition of the same MRM transition to the list, but with one or more different mobility device parameter values. Since, for the majority of the acquisition time, only one MRM transition for each compound is being acquired, this method enables the monitoring of a larger number of compounds across a wide range of mobility device parameter values during a single liquid chromatography run or a single injection.

Mobility device parameters that vary with different compounds or ions include, for example, the compensation voltage (CoV). CoV is a direct current (DC) potential that corrects drift trajectory, for example. One skilled in the art can appreciate that there are many different mobility device parameters that vary with different compounds or ions. However, in order to increase the number of compounds that can be interrogated during a single liquid chromatography run or a single injection, the parameters used with MRM triggered MRM must be adjustable in a short amount of time.

In various embodiments, MRM triggered MRM, with different mobility device parameter values, is used to multiplex the optimization of mobility device parameter values. For example, an original or primary MRM transition is set with wide CoV steps and secondary MRM transitions are triggered with fine CoV steps. Tertiary CoV steps or beyond could also be used for even finer mapping if required, or multiple injections could be performed for finer CoV mapping.

As described above in a preferred embodiment, MRM triggered MRM is used to trigger MRM transitions for the same compound that use different device parameter values for a device external to the mass spectrometer, such as a DMS device. In other words, the device parameter values are not for the mass spectrometer itself.

In various alternative embodiments, MRM triggered MRM can be used to trigger MRM transitions of a compound that use different device parameter values for the mass spectrometer itself. For example, MRM transitions that all have the same precursor ion and product ion can be triggered with different collision energy values for the collision cell of the mass spectrometer. Similarly as described above, MRM triggered MRM can then be used to determine the optimal collision energy for a compound.

Steps of Workflow

First, a user tunes 1-3 MRM transitions for each compound of interest, which act as the primary detection MRM transitions for the target compounds, for example. Each primary or original MRM transition for the compound of interest is placed on the MRM cycle list for compounds with the mobility device parameter value set to effectively turn the mobility device off. For example, with the mobility device set to non-resolving and the CoV set to 0.

In alternative embodiments, each primary or original MRM transition for the compound of interest is placed on the MRM cycle list for compounds two or more times with different mobility device parameter values that span a range of values. Compounds can include, but are not limited to, peptides as described in the following examples. An exemplary CoV range for a peptide is 5-25 at 3500 V, so the primaries could be set to 9, 17, and 25. It may be faster to start with nonzero mobility device parameter values if, for example, it takes much more time to turn the mobility device on rather than to go from a low level on to a higher level on, or if the mobility device provides low and high resolution modes.

Second, in the same method, secondary MRM transitions are set to trigger when signal is detected in the first primary MRM transition and exceeds a specified intensity threshold using MRM triggered MRM. The secondary MRM transitions, for example, are the same Q1 and Q3 masses and there are two or more transitions, each at a different CoV values. Essentially, when a primary MRM transition triggers, it sets off a mini-CoV ramp. For example, one primary MRM transition for a peptide is set to a CoV of 9 and triggers a set of secondary MRM transitions of the same Q1/Q3 with CoV values at 5, 6, 7, 8, 10, 11, 12, and 13. The intensity comparison between these secondary MRM transitions determines the optimal CoV for that peptide. A different primary peptide that has an intensity in a primary MRM transition at a CoV of 25 can also trigger secondary MRM transitions of 21, 22, 23, 24, 26, 27, 28, and 29 and the optimal CoV for this peptide is also determined. In this way, a much larger number of analytes can be interrogated during a single LC run.

In another example of a mini-CoV ramp, three primary MRM transitions are set for each specific peptide with CoV values of 9, 17 and 25. If signal is observed in the primary MRM transition with CoV value of 17 for peptide A, it triggers a set of secondary MRM transitions for peptide A with CoV values of 14, 15, 16, 18, 19, and 20. The intensity comparison between these secondary MRM transitions determines the optimal CoV for peptide A. If signal is observed in the primary MRM transition with CoV value 25 for peptide A, then it triggers secondary MRM transitions with CoV values of 21, 22, 23, 24, 26, 27, 28, and 29. The intensity comparison between these secondary MRM transitions determines the optimal CoV for peptide A. This is done for each compound and allows for the interrogation of many analytes across a broader CoV space.

In another example, the mini-CoV ramp could be an iterative process. In the first injection of the process, three primary MRM transitions are set for each specific peptide with CoV values of 9, 17 and 25. If signal is observed in the primary MRM transition with CoV value of 17 for compound A, it triggers a set of secondary MRM transitions for compound A with CoV values of 15 and 19. The intensity comparison between these secondary MRM transitions determines the center point for CoV optimization in the next injection in the process. In the second injection, the CoV value that had the largest signal (either 15, 17, 19) is used for the primary MRM transition for the compound. When signal is observed, it triggers a set of secondary MRM transitions that are set to be finer steps around the primary MRM transition CoV. As an example, for compound A the MRM transition with CoV 15 had the highest signal and therefore becomes the primary MRM for the iterative second injection. In the second injection, signal detection in the primary MRM transition triggers secondary MRM transitions with CoV values of 13, 13.5, 14, 14.5, 15.5, 16, 16.5, and 17. Smaller steps are taken for more accurate value determination.

In various embodiments, the chromatographic retention time of the peptides of interest is pre-determined and the CoV ramping experiment using MRM triggered MRM is done in a time scheduled manner to further enhance the capacity of the method.

In various embodiments, during the data processing, the signal heights for all of the secondary MRM transitions are compared and the optimum CoV values determined and integrated into the final MRM assay.

MRM triggered MRM with different mobility device parameter values provides much higher throughput and efficiency in CoV mapping when developing assays with large numbers of analytes.

MRM Triggered MRM System to Control a Mobility Device

Figure 2:
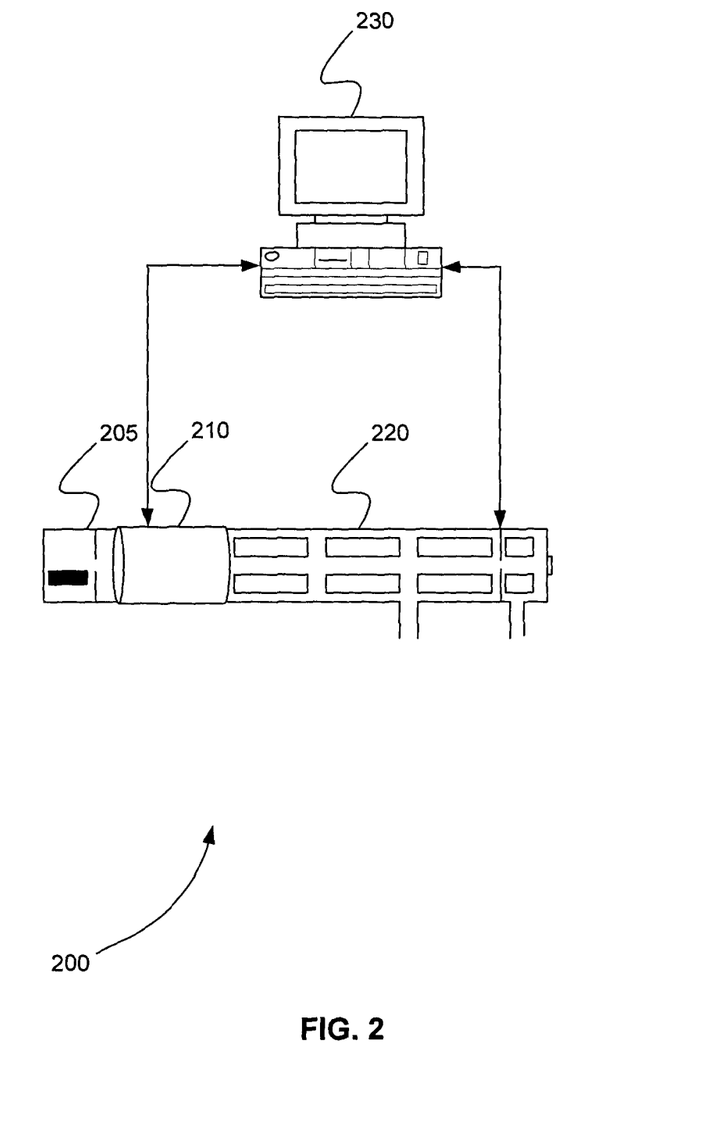
FIG. 2 is a schematic diagram showing a system for performing multiple reaction monitoring (MRM) triggered MRM that triggers MRM transitions that use different differential mobility separation (DMS) device parameter values for the same compound, in accordance with various embodiments

FIG. 2 is a schematic diagram showing a system 200 for performing MRM triggered MRM that triggers MRM transitions that use different mobility device parameter values for the same compound, in accordance with various embodiments. System 200 includes ion source 205, mobility device 210, mass spectrometer 220, and processor 230.

Ion source 205 ionizes a sample producing an ion beam. The system can also include a sample introduction device (not shown) that presents the sample to the ion source. The sample introduction device can provide a sample to ion source 205 using one of a variety of techniques. These techniques include, but are not limited to, gas chromatography (GC), liquid chromatography (LC), capillary electrophoresis (CE), or flow injection analysis (FIA).

Mobility device 210 receives the ion beam from ion source 205. Mobility device 210 is adapted to accept a mobility device parameter value that causes mobility device 210 to select ions from the ion beam based on the mobility device parameter value. Mobility device 210 is a DMS device, for example. A DMS device can include, but is not limited to, a SelexION™ device, for example. A mobility device parameter is the compensation voltage (CoV), for example.

Mass spectrometer 220 is a tandem mass spectrometer and can include one or more physical mass filters and one or more physical mass analyzers. A mass analyzer of mass spectrometer 220 can include, but is not limited to, a time-of-flight (TOF), quadrupole, an ion trap, a linear ion trap, an orbitrap, or a Fourier transform mass analyzer. Mass spectrometer 220 that is adapted to receive ions from mobility device 210 and perform MRM scans on the received ions.

Processor 230 can be, but is not limited to, a computer, microprocessor, or any device capable of sending and receiving control information and data to and from mobility device 210 and mass spectrometer 220 and processing data. Processor 230 is in communication with mobility device 210 and mass spectrometer 220.

Processor 230 receives one or more MRM precursor ion to product ion transitions for one or more compounds from a user. As a result, processor 230 receives a plurality of primary MRM transitions from the user. For each transition of the plurality of primary MRM transitions, processor 230 creates and stores a plurality of secondary MRM precursor ion to product ion transitions that each include the same precursor ion to product ion transition as the primary MRM transition but have different mobility device parameter values. The different mobility device parameter values for the plurality of secondary MRM transitions for each transition of the plurality of primary MRM transitions span a range of mobility device parameter values. The mobility device parameter values spanning the range can be equally spaced or spaced according to known distribution of parameters, for example.

Processor 230 creates and stores an MRM cycle list that initially includes the plurality of primary MRM transitions and an initial mobility device parameter value for each transition of the plurality of primary MRM transitions. The initial mobility device parameter value for each transition of the plurality of primary MRM transitions turns mobility device 210 off, for example. In various alternative embodiments, the initial mobility device parameter value for each transition of the plurality of primary MRM transitions sets mobility device 210 to a low resolution level.

Processor 230 sends control information, including the MRM cycle list, to mobility device 210 and mass spectrometer 220. The control information instructs mobility device 210 and mass spectrometer 220 to interrogate each MRM transition on the MRM cycle list within an MRM cycle of the mass spectrometer. For each MRM transition, the mobility device parameter value is applied to mobility device 210 and mass spectrometer 220 performs an MRM scan.

Processor 230 receives a product ion intensity value from mass spectrometer 220 for each MRM transition. Processor 230 stores the product ion intensity value with a primary or secondary MRM transition represented by the MRM transition.

If a product ion intensity value of an MRM transition exceeds a threshold value and the MRM transition is a primary MRM transition, processor 230 adds a plurality of secondary MRM transitions of the primary MRM transition to the MRM cycle list. Processor 230 repeats the steps above starting with sending control information to mobility device 210 and mass spectrometer 220. Processor 230 repeats the steps above for each additional cycle until the number of cycles exceeds a limit, for example.

In various embodiments, mobility device 210 includes a modifier and the mobility device parameter values are dependent on the modifier. The modifier is a modifier gas, for example.

In various embodiments, processor 230 further determines an optimal mobility device parameter value for a compound. Processor 230 compares any product ion intensity values stored for secondary MRM transitions. Processor 230 selects a mobility device parameter value of the secondary MRM transition with the greatest intensity value as the optimal mobility device parameter value for the compound, for example.

MRM Triggered MRM Method to Control a Mobility Device

Figure 3:
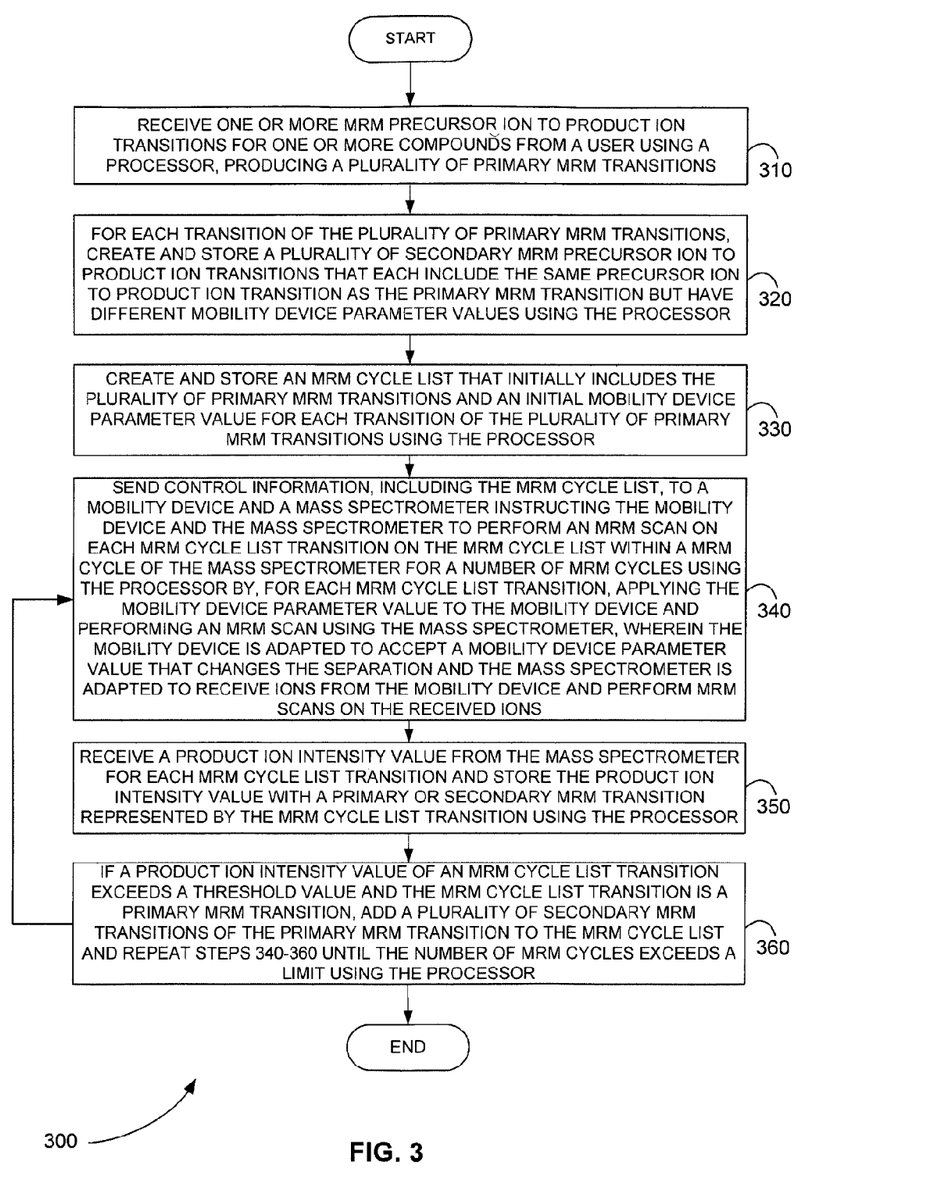
FIG. 3 is an exemplary flowchart showing a method for performing MRM triggered MRM that triggers MRM transitions that use different mobility device parameter values for the same compound, in accordance with various embodiments.

FIG. 3 is an exemplary flowchart showing a method 300 for performing MRM triggered MRM that triggers MRM transitions that use different mobility device parameter values for the same compound, in accordance with various embodiments.

In step 310 of method 300, one or more MRM precursor ion to product ion transitions for one or more compounds are received from a user using a processor. A plurality of primary MRM transitions are, therefore, received from the user.

In step 320, for each transition of the plurality of primary MRM transitions, a plurality of secondary MRM precursor ion to product ion transitions are created and stored using the processor. Each secondary MRM transition includes the same precursor ion to product ion transition as the primary MRM transition, but has a different mobility device parameter value.

In step 330, an MRM cycle list that initially includes the plurality of primary MRM transitions and an initial mobility device parameter value for each transition of the plurality of primary MRM transitions is created and stored using the processor.

In step 340, control information, including the MRM cycle list, is sent to a mobility device and a mass spectrometer using the processor. The control information instructs the mobility device and the mass spectrometer to interrogate each MRM transition on the MRM cycle list within an MRM cycle of the mass spectrometer. For each MRM transition, the mobility device parameter value is applied to the mobility device and an MRM scan is performed using the mass spectrometer. The mobility device receives an ion beam from an ion source that ionizes a sample. The mobility device is adapted to accept a mobility device parameter value that causes the mobility device to select ions from the ion beam based on the mobility device parameter value. The mass spectrometer is adapted to receive ions from the mobility device and perform MRM scans on the received ions.

In step 350, a product ion intensity value is received from the mass spectrometer for each MRM transition and the product ion intensity value is stored with a primary or secondary MRM transition represented by the MRM transition using the processor.

In step 360, if a product ion intensity value of an MRM transition exceeds a threshold value and the MRM transition is a primary MRM transition, a plurality of secondary MRM transitions of the primary MRM transition are added to the MRM cycle list and steps 340-360 are repeated using the processor.

In various embodiments, an optimum mobility device parameter for a compound is found iteratively across multiple runs or injections, as described above. For example, steps (310)-(360) are performed for a first injection. A product ion intensity value from a triggered primary MRM transition is found that exceeds the threshold value. A plurality of secondary MRM transitions of the triggered primary MRM transition are added to the MRM cycle list, producing product ion intensity data for the triggered primary MRM transition with different mobility device parameters.

The product ion intensity data is compared to determine a mobility device parameter that produces the largest product ion intensity. The determined mobility device parameter is set for the triggered primary MRM transition in a second MRM cycle list for a second injection. A new plurality of secondary MRM transitions is also stored for the triggered primary MRM transition for the second injection. The new plurality of secondary MRM transitions have, for example, smaller differences between their mobility device parameter values than the previous plurality of secondary MRM transitions stored for the triggered primary MRM transition for the first injection. The triggered primary MRM transition with an updated mobility device parameter is added to the second MRM cycle list and the new plurality of secondary MRM transitions are stored for the second injection. Steps (310)-(360) are then performed for the second injection. These steps can be performed iteratively for additional injections until a desired level of accuracy is achieved for the mobility device parameter for the triggered primary MRM transition.

MRM Triggered MRM Computer Program Product to Control a Mobility Device

In various embodiments, computer program products include a non-transitory and tangible computer-readable storage medium whose contents include a program with instructions being executed on a processor so as to perform a method for performing MRM triggered MRM that triggers MRM transitions that use different mobility device parameter values for the same compound. This method is performed by a system that includes one or more distinct software modules.

Figure 4:
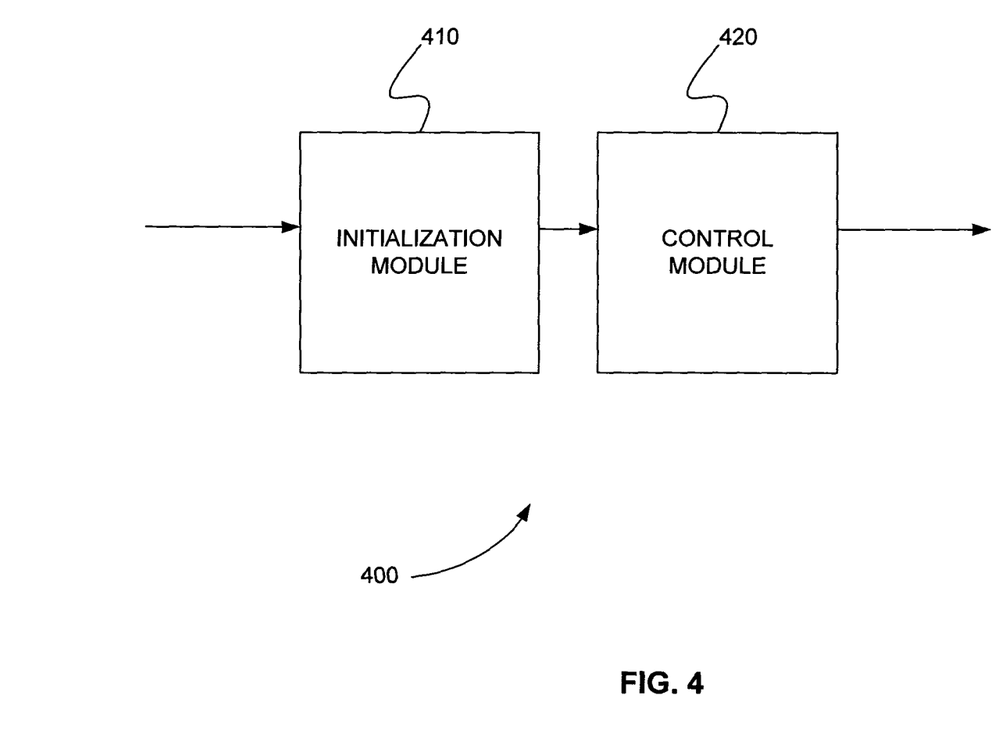
FIG. 4 is a schematic diagram of a system that includes one or more distinct software modules that perform a method for performing MRM triggered MRM that triggers MRM transitions that use different mobility device parameter values for the same compound, in accordance with various embodiments.

FIG. 4 is a schematic diagram of a system 400 that includes one or more distinct software modules that perform a method for performing MRM triggered MRM that triggers MRM transitions that use different mobility device parameter values for the same compound, in accordance with various embodiments. System 400 includes an initialization module 410 and a control module 420.

Initialization module 410 receives one or more MRM precursor ion to product ion transitions for one or more compounds from a user. As a result, initialization module 410 receives a plurality of primary MRM transitions from the user. For each transition of the plurality of primary MRM transitions, initialization module 410 creates and stores a plurality of secondary MRM precursor ion to product ion transitions that each include the same precursor ion to product ion transition as the primary MRM transition but have different mobility device parameter values. Initialization module 410 creates and stores an MRM cycle list that initially includes the plurality of primary MRM transitions and an initial mobility device parameter value for each transition of the plurality of primary MRM transitions.

Control module 420 sends control information, including the MRM cycle list, to a mobility device and a mass spectrometer. The control information instructs the mobility device and the mass spectrometer to interrogate each MRM transition on the MRM cycle list within an MRM cycle of the mass spectrometer. For each MRM transition, the mobility device parameter value is applied to the mobility device, and the mass spectrometer performs an MRM scan. The mobility device receives an ion beam from an ion source that ionizes a sample. The mobility device is adapted to accept a mobility device parameter value that causes the mobility device to select ions from the ion beam based on the mobility device parameter value. The mass spectrometer is adapted to receive ions from the mobility device and perform MRM scans on the received ions.

Control module 420 receives a product ion intensity value from the mass spectrometer for each MRM transition. Control module 420 stores the product ion intensity value with a primary or secondary MRM transition represented by the MRM transition.

If a product ion intensity value of an MRM transition exceeds a threshold value and the MRM transition is a primary MRM transition, control module 420 adds a plurality of secondary MRM transitions of the primary MRM transition to the MRM cycle list. Control module 420 repeats the steps above starting with sending control information to the mobility device and the mass spectrometer.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

What is claimed is:

1. A system for performing multiple reaction monitoring (MRM) triggered MRM that triggers MRM transitions that use different mobility device parameter values for the same compound, comprising:
    an ion source that ionizes a sample producing an ion beam;
    a mobility device that receives the ion beam from the ion source and is adapted to accept a mobility device parameter value that causes the mobility device to select ions from the ion beam based on the mobility device parameter value;
    a mass spectrometer that is adapted to receive selected ions from the mobility device and perform MRM scans on the received ions; and
    a processor in communication with the mass spectrometer and the mobility device that
        (a) receives one or more MRM precursor ion to product ion transitions for one or more compounds from a user, producing a plurality of primary MRM transitions,
        (b) for each transition of the plurality of primary MRM transitions, creates and stores a plurality of secondary MRM precursor ion to product ion transitions that each include the same precursor ion to product ion transition as the primary MRM transition but have different mobility device parameter values,
        (c) creates and stores an MRM cycle list that initially includes the plurality of primary MRM transitions and an initial mobility device parameter value for each transition of the plurality of primary MRM transitions,
        (d) sends control information, including the MRM cycle list, to the mobility device and the mass spectrometer instructing the mobility device and the mass spectrometer to interrogate each MRM transition on the MRM cycle list within an MRM cycle of the mass spectrometer by, for each MRM transition, applying the mobility device parameter value to the mobility device and performing an MRM scan using the mass spectrometer,
        (e) receives a product ion intensity value from the mass spectrometer for each MRM transition and stores the product ion intensity value with a primary or secondary MRM transition represented by the MRM transition, and
        (f) if a product ion intensity value of an MRM transition exceeds a threshold value and the MRM transition is a primary MRM transition, adds a plurality of secondary MRM transitions of the primary MRM transition to the MRM cycle list and repeats steps (d)-(f).

2. The system of claim 1, wherein the mobility device parameter comprises compensation voltage (CoV).

3. The system of claim 1, wherein an initial mobility device parameter value for each transition of the plurality of primary MRM transitions turns the mobility device off.

4. The system of claim 1, wherein an initial mobility device parameter value for each transition of the plurality of primary MRM transitions sets the mobility device to a low resolution level.

5. The system of claim 1, wherein different mobility device parameter values for the plurality of secondary MRM transitions for each transition of the plurality of primary MRM transitions span a range of mobility device parameter values.

6. The system of claim 1, wherein the mobility device parameter values spanning the range are equally spaced.

7. The system of claim 1, wherein the mobility device includes a modifier and the mobility device parameter values are dependent on the modifier.

8. The system of claim 1, wherein the processor further determines an optimal mobility device parameter value for a compound by
    comparing any product ion intensity values stored for secondary MRM transitions and selecting a mobility device parameter value of a secondary MRM transition with the greatest intensity value as the optimal mobility device parameter value for the compound.

9. A method for performing multiple reaction monitoring (MRM) triggered MRM that triggers MRM transitions that use different mobility device parameter values for the same compound, comprising:
    (a) receiving one or more MRM precursor ion to product ion transitions for one or more compounds from a user using a processor, producing a plurality of primary MRM transitions;
    (b) for each transition of the plurality of primary MRM transitions, creating and storing a plurality of secondary MRM precursor ion to product ion transitions that each include the same precursor ion to product ion transition as the primary MRM transition but have different mobility device parameter values using the processor;
    (c) creating and storing an MRM cycle list that initially includes the plurality of primary MRM transitions and an initial mobility device parameter value for each transition of the plurality of primary MRM transitions using the processor;
(d) sending control information, including the MRM cycle list, to a mobility device and a mass spectrometer instructing the mobility device and the mass spectrometer to interrogate each MRM transition on the MRM cycle list within an MRM cycle of the mass spectrometer using the processor by, for each MRM transition, applying the mobility device parameter value to the mobility device and performing an MRM scan using the mass spectrometer, wherein the mobility device receives an ion beam from an ion source that ionizes a sample and is adapted to accept a mobility device parameter value that causes the mobility device to select ions from the ion beam based on the mobility device parameter value, and wherein the mass spectrometer is adapted to receive selected ions from the mobility device and perform MRM scans on the received ions;
(e) receiving a product ion intensity value from the mass spectrometer for each MRM transition and storing the product ion intensity value with a primary or secondary MRM transition represented by the MRM transition using the processor; and
(f) if a product ion intensity value of an MRM transition exceeds a threshold value and the MRM transition is a primary MRM transition, adding a plurality of secondary MRM transitions of the primary MRM transition to the MRM cycle list and repeating steps (d)-(f).

10. The method of claim 9, wherein the mobility device parameter comprises compensation voltage (CoV).

11. The method of claim 9, wherein an initial mobility device parameter value for each transition of the plurality of primary MRM transitions turns the mobility device off.

12. The method of claim 9, wherein an initial mobility device parameter value for each transition of the plurality of primary MRM transitions sets the mobility device to a low resolution level.

13. The method of claim 9,
wherein steps (a)-(f) are performed for a first injection, a product ion intensity value from a triggered primary MRM transition exceeds the threshold value and a plurality of secondary MRM transitions of the triggered primary MRM transition are added to the MRM cycle list, producing product ion intensity data for the triggered primary MRM transition with different mobility device parameters and
further comprising comparing the product ion intensity data, determining a mobility device parameter that produces the largest product ion intensity from the comparison, setting the determined mobility device parameter for the new primary MRM transition a second MRM cycle list for a second injection, storing a new plurality of secondary MRM transitions for the triggered primary MRM transition for the second injection, wherein the new plurality of secondary MRM transitions have smaller differences between their mobility device parameter values than a previous plurality of secondary MRM transitions stored for the triggered primary MRM transition for the first injection, adding the triggered primary MRM transition to the second MRM cycle list, and performing steps (a)-(f) for the second injection.

14. The method of claim 9, further comprising determining an optimal mobility device parameter value for a compound by comparing any product ion intensity values stored for secondary MRM transitions and selecting a mobility device parameter value of a secondary MRM transition with the greatest intensity value as the optimal mobility device parameter value for the compound.

15. A computer program product, comprising a non-transitory and tangible computer-readable storage medium whose contents include a program with instructions being executed on a processor so as to perform a method for performing multiple reaction monitoring (MRM) triggered MRM that triggers MRM transitions that use different mobility device parameter values for the same compound, the method comprising:
(a) providing a system, wherein the system comprises one or more distinct software modules, and wherein the distinct software modules comprise an initialization module and a control module;
(b) receiving one or more MRM precursor ion to product ion transitions for one or more compounds from a user using the initialization module, producing a plurality of primary MRM transitions;
(c) for each transition of the plurality of primary MRM transitions, creating and storing a plurality of secondary MRM precursor ion to product ion transitions that each include the same precursor ion to product ion transition as the primary MRM transition but have different mobility device parameter values using the initialization module;
(d) creating and storing an MRM cycle list that initially includes the plurality of primary MRM transitions and an initial mobility device parameter value for each transition of the plurality of primary MRM transitions using the initialization module;
(e) sending control information, including the MRM cycle list, to a mobility device and a mass spectrometer instructing the mobility device and the mass spectrometer to interrogate each MRM transition on the MRM cycle list within an MRM cycle of the mass spectrometer using the control module by, for each MRM transition, applying the mobility device parameter value to the mobility device and performing an MRM scan using the mass spectrometer, wherein the mobility device receives an ion beam from an ion source that ionizes a sample and is adapted to accept a mobility device parameter value that causes the mobility device to select ions from the ion beam based on the mobility device parameter value and wherein the mass spectrometer is adapted to receive selected ions from the mobility device and perform MRM scans on the received ions;
(f) receiving a product ion intensity value from the mass spectrometer for each MRM transition and storing the product ion intensity value with a primary or secondary MRM transition represented by the MRM transition using the control module; and
(g) if a product ion intensity value of an MRM transition exceeds a threshold value and the MRM transition is a primary MRM transition, adding a plurality of secondary MRM transitions of the primary MRM transition to the MRM cycle list and repeating steps (e)-(g) using the control module.

16. The computer program product of claim 15, wherein the mobility device parameter comprises compensation voltage (CoV).

17. The computer program product of claim 15, wherein an initial mobility device parameter value for each transition of the plurality of primary MRM transitions turns the mobility device off.

18. The computer program product of claim 15, wherein an initial mobility device parameter value for each transition of the plurality of primary MRM transitions sets the mobility device to a low resolution level.

19. The computer program product of claim 15,
wherein steps (a)-(f) are performed for a first injection, a product ion intensity value from a triggered primary MRM transition exceeds the threshold value and a plurality of secondary MRM transitions of the triggered primary MRM transition are added to the MRM cycle list, producing product ion intensity data for the triggered primary MRM transition with different mobility device parameters and
wherein the method further comprises comparing the product ion intensity data, determining a mobility device parameter that produces the largest product ion intensity from the comparison, setting the determined mobility device parameter for the new primary MRM transition a second MRM cycle list for a second injection, storing a new plurality of secondary MRM transitions for the triggered primary MRM transition for the second injection, wherein the new plurality of secondary MRM transitions have smaller differences between their mobility device parameter values than a previous plurality of secondary MRM transitions stored for the triggered primary MRM transition for the first injection, adding the triggered primary MRM transition to the second MRM cycle list, and performing steps (a)-(f) for the second injection.

20. The computer program product of claim 15, wherein the method further comprises determining an optimal mobility device parameter value for a compound by
comparing any product ion intensity values stored for secondary MRM transitions and selecting a mobility device parameter value of a secondary MRM transition with the greatest intensity value as the optimal mobility device parameter value for the compound.

\* \* \* \* \*